United States Patent [19]
Cosmescu

[11] Patent Number: 6,149,648
[45] Date of Patent: Nov. 21, 2000

[54] ELECTRO-SURGICAL UNIT-ARGON BEAM COAGULATOR PENCIL APPARATUS AND METHOD FOR OPERATING SAME

[76] Inventor: Ioan Cosmescu, 14449 N. 22 St., Phoenix, Ariz. 85022

[21] Appl. No.: 08/971,011

[22] Filed: Nov. 14, 1997

Related U.S. Application Data

[60] Division of application No. 08/500,045, Jul. 10, 1995, Pat. No. 5,693,044, which is a continuation-in-part of application No. 08/196,802, Feb. 15, 1994, Pat. No. 5,431,650, which is a continuation of application No. 07/989,238, Dec. 11, 1992, abandoned.

[51] Int. Cl.[7] .................................................... A61B 18/18
[52] U.S. Cl. .................................. 606/42; 606/45; 606/49
[58] Field of Search ........................... 606/34, 39, 40–42, 606/45–52; 604/21, 22, 35

[56] References Cited

U.S. PATENT DOCUMENTS

| 5,085,657 | 2/1992 | Ben-Simhon | 606/42 |
|---|---|---|---|
| 5,154,709 | 10/1992 | Johnson | 606/45 |
| 5,197,963 | 3/1993 | Parins | 606/46 |
| 5,234,428 | 8/1993 | Kaufman | 606/45 |
| 5,318,565 | 6/1994 | Kuriloff et al. | 606/49 |
| 5,720,745 | 2/1998 | Farin et al. | 60/49 |

*Primary Examiner*—Linda C. M. Dvorak
*Assistant Examiner*—Bryan K. Yarnell
*Attorney, Agent, or Firm*—Snell & Wilmer, LLP

[57] ABSTRACT

An electro-surgical unit (ESU)-Argon beam coagulator pencil apparatus and method for operating the same is disclosed where the ESU-Argon beam coagulator pencil apparatus includes a telescoping device which is coupled to a cutting means, a coagulation means, and a smoke evacuation means. This apparatus enables a surgeon to vary the length of the cutting or coagulation means without interrupting the smoke evacuation means of the device. A locking means may also be included to lock the cutting and/or coagulation means at a desired length.

22 Claims, 5 Drawing Sheets

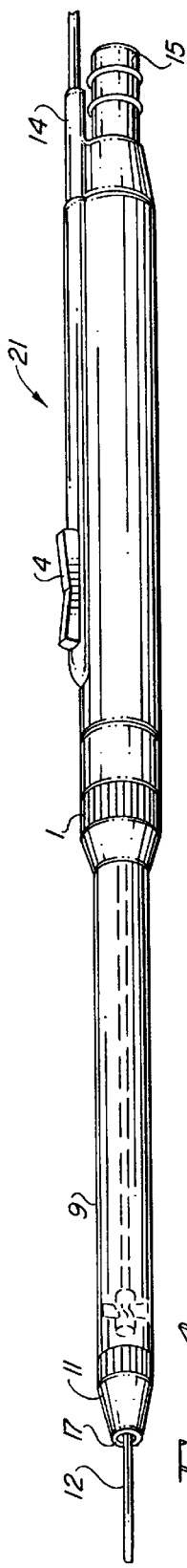
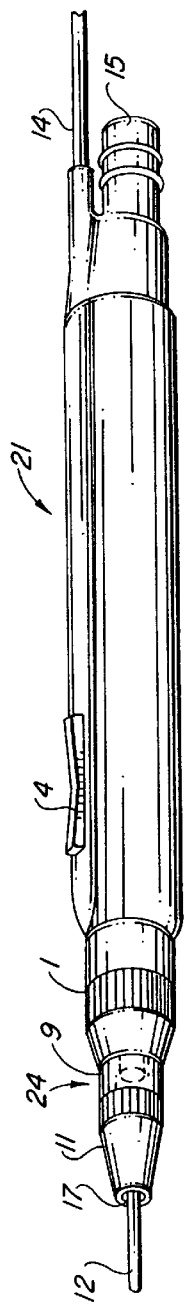
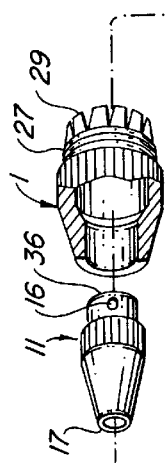
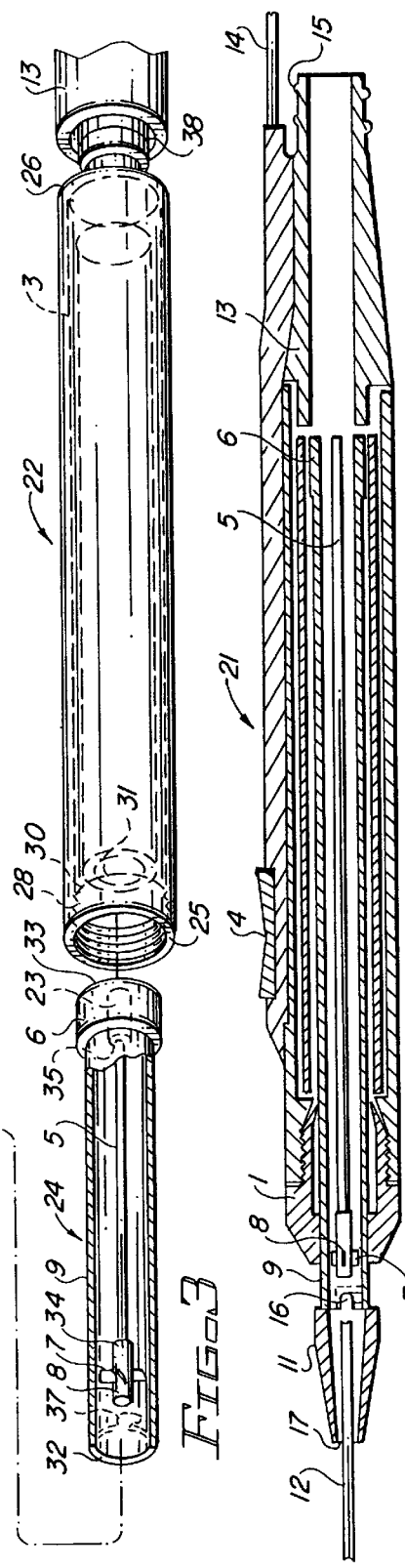

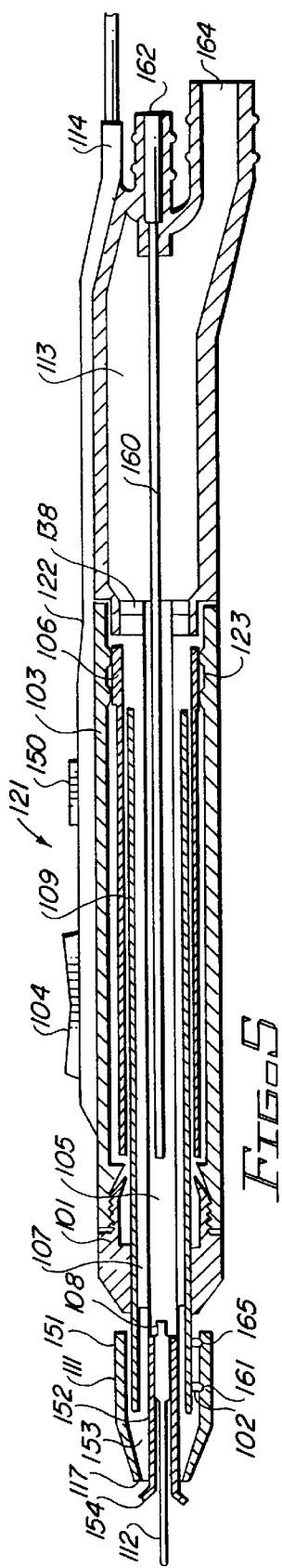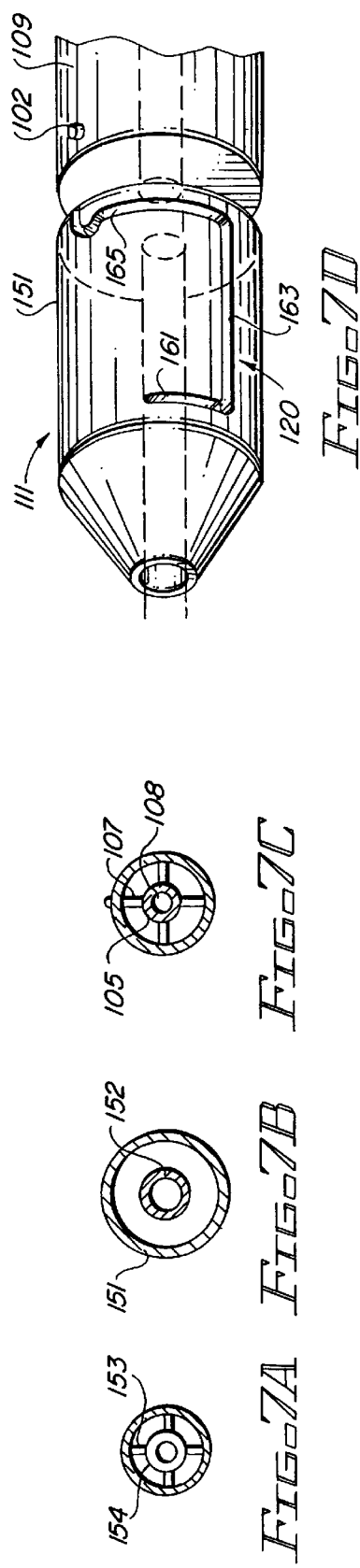

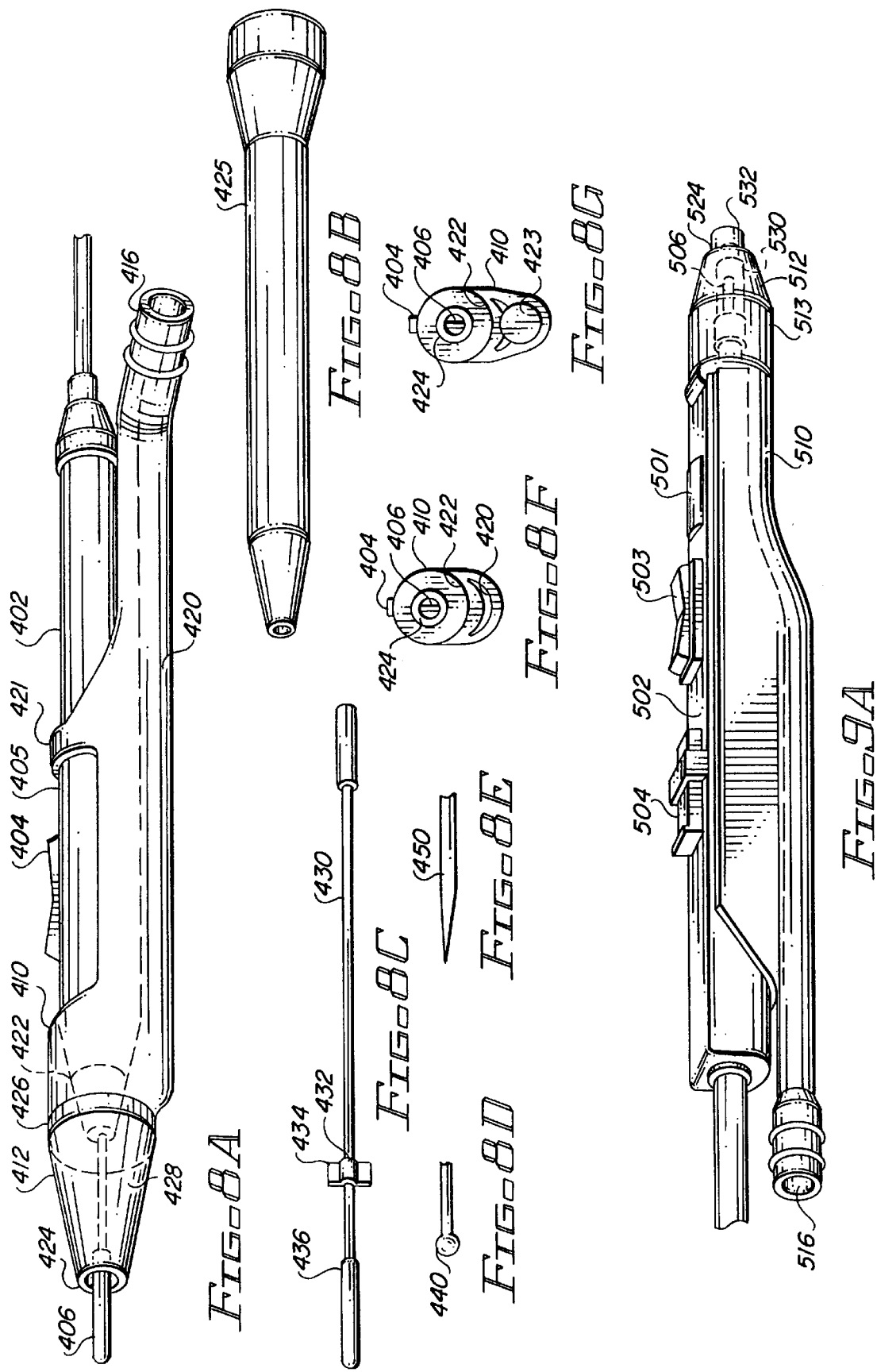

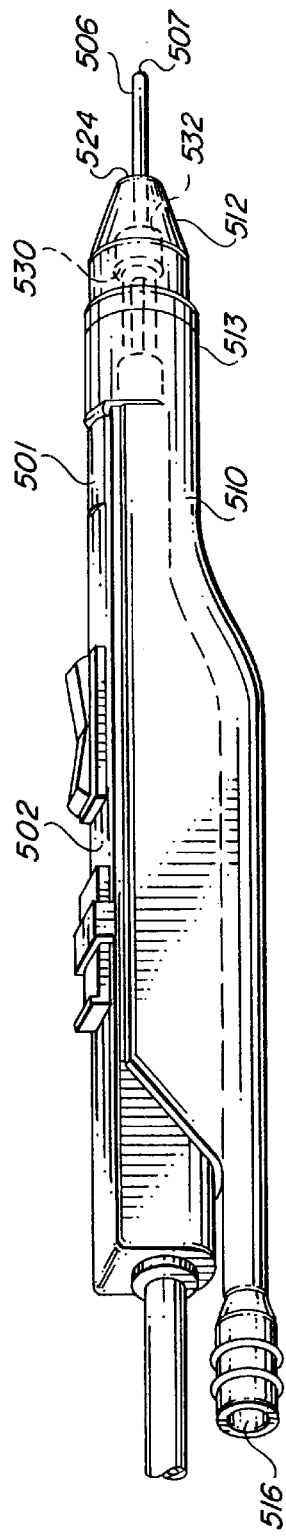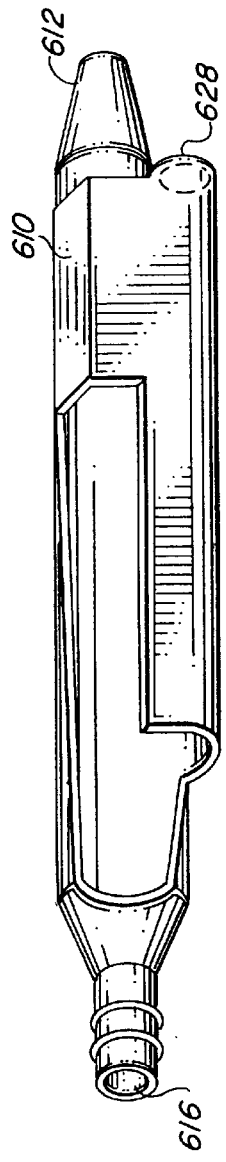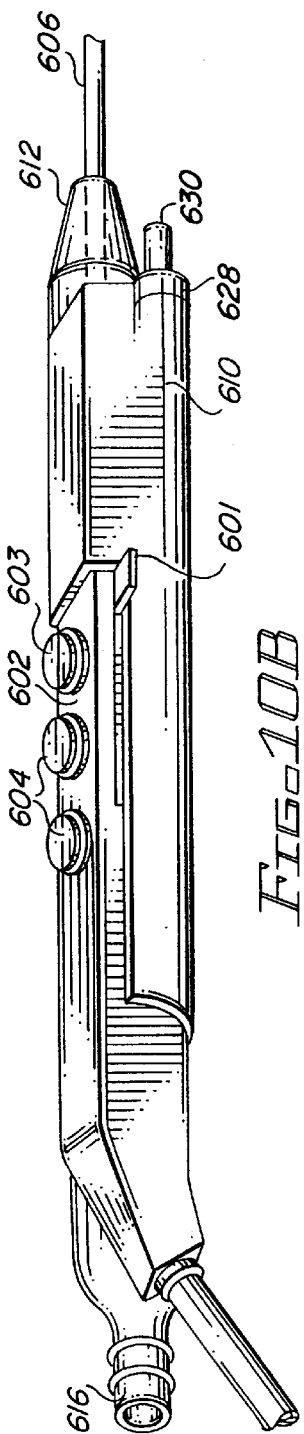

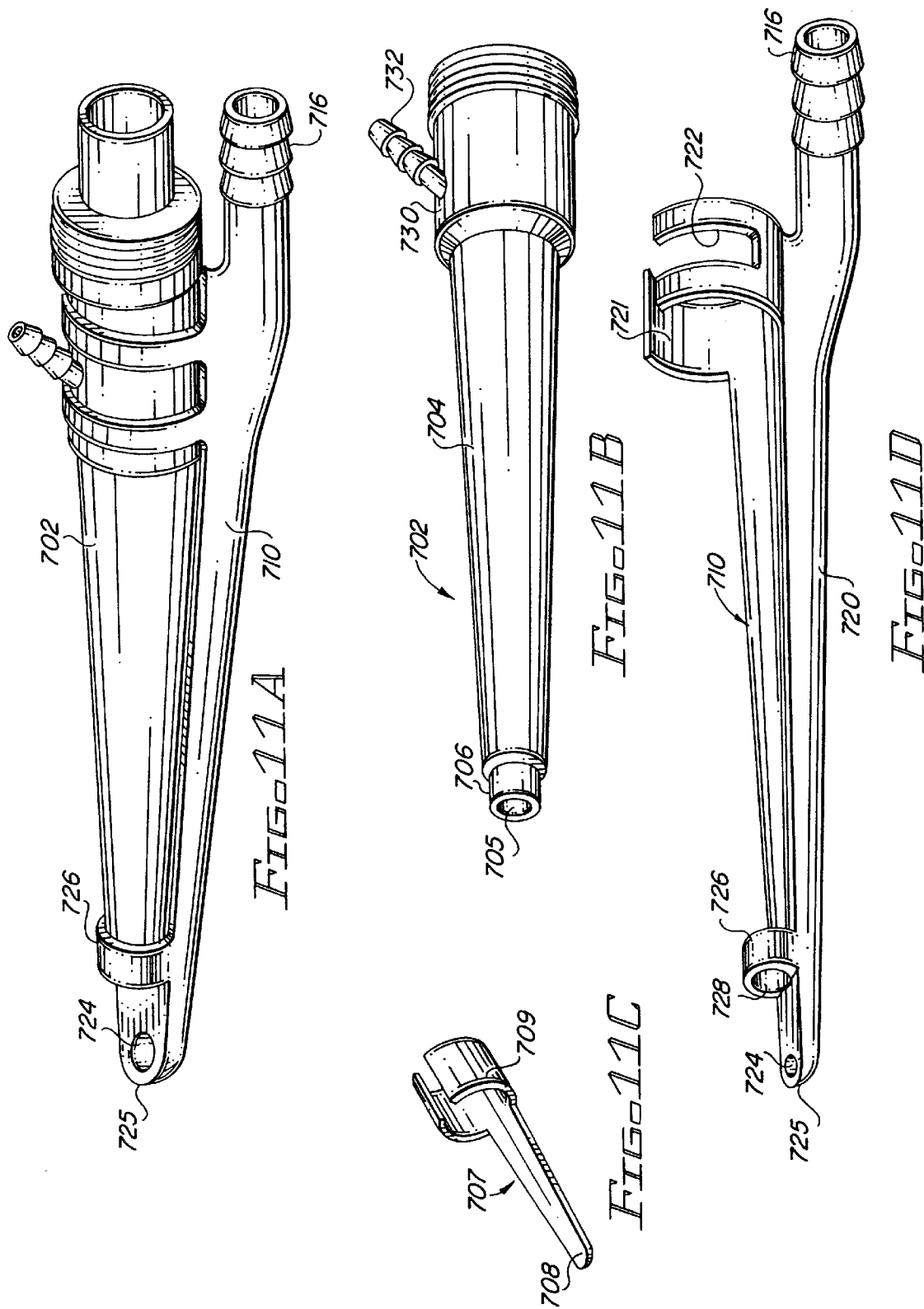

ELECTRO-SURGICAL UNIT-ARGON BEAM COAGULATOR PENCIL APPARATUS AND METHOD FOR OPERATING SAME

RELATED APPLICATION

This patent application is related to and incorporates herein by reference my prior filed U.S. patent application entitled "A TELESCOPIC SURGICAL DEVICE AND METHOD THEREFOR," filed on Jul. 10, 1995 under Ser. No. 08/500,045, now U.S. Pat. No. 5,693,044, and is a Divisional patent application thereof, which is a continuation-in-part of my U.S. patent application Ser. No. 08/196,802 under the same title filed on Feb. 15, 1994, now U.S. Pat. No. 5,431,650, which is a continuation of Ser. No. 07/989,238, filed Dec. 11, 1992, now abandoned.

BACKGROUND OF THE INVENTION

1. Field of the Invention

This invention relates generally to electro-surgical unit (ESU) pencil apparatus and, more specifically, to electro-surgical pencil apparatus with a variable length electrode and smoke evacuation means, and methods therefor.

2. Description of the Related Art

In the past, when it was desired to change the length of the electrode of an ESU pencil, the electrode would be taken out, and replaced with another of different length. This created a number of problems. First, the electrodes are available only in two or three standard sizes. Thus, if the length desired by the surgeon was different from what was commercially available, then the surgeon would have to compromise and make do with the closest available size. Second, changing electrodes during an operation wastes time. Also, changing electrodes has an economic cost. And third, when an extended length electrode is used, the opening to the smoke evacuation conduit is often situated too far from the operation site to be effective. This meant that a special smoke evacuation shroud had to be used with the extended electrode, thereby further increasing the cost of the operation.

Also, in the past, it had not been possible to use an ESU pencil while operating both an argon beam coagulator and a smoke evacuation system simultaneously. This was true because the operation of the smoke evacuation system would interrupt the flow of the argon beam before it reached the site of the operation and deflect it directly into the smoke evacuation conduit.

Further, in order to evacuate the smoke from the surgical field in laparatomy when an ESU pencil handpiece without a smoke collector is used for cutting and coagulation, several methods have been used but their performances have not been satisfactory. In order to be efficient, the shroud which performs the smoke collection function must be as close as possible to the operating tip of the ESU pencil where the smoke is generated. But, this solution as embodied in prior art tended to obstruct the surgeon's view of the operation site. Accordingly, there was a need for an improved handpiece and shroud arrangement which provided for efficient smoke collection without obstructing the surgeon's view of the surgical site.

Therefore, there existed a need for an improved, reusable ESU pencil that allowed telescoping the electrode assembly containing a standard size electrode, and provided efficient smoke evacuation at all positions of the telescopic electrode assembly. Further, these improvements needed to be incorporated into an ESU-argon beam coagulator pencil.

SUMMARY OF THE INVENTION

An object of this invention is to provide an ESU pencil apparatus in which the distance between the operating tip of the electrode and the handpiece is adjustable to the surgeon's desired length, and methods therefor.

Another object of this invention is to provide a smoke evacuator that functions effectively irrespective of the distance between the operating tip of the electrode and the handpiece of the ESU pencil, and method therefor.

Another object of this invention is to provide an ESU pencil apparatus that is substantially reusable, and methods therefor.

Another object of this invention is to provide an ESU pencil apparatus that uses a vortex to increase the efficiency of smoke evacuation, and methods therefor.

Another object of this invention is to provide an ESU pencil apparatus where the distance between the operating tip of the electrode and the intake to the smoke evacuation conduit is adjustable, thereby enabling the surgeon to optimize the exhaust suction and visibility of the operating site, and methods therefor.

Another object of this invention is to provide an ESU pencil apparatus that combines an argon gas coagulator with a smoke evacuation system, and methods therefor.

Another object of this invention is to provide an improved smoke evacuation shroud apparatus for use with, but not limited to, an electro-surgical, an ESU-argon beam coagulator pencil, or a laser surgical unit, and methods therefor.

Another object of this invention is to provide an improved smoke evacuation shroud apparatus for use with, but not limited to, a laser surgical, an electro-surgical, or an ESU-argon beam coagulator pencil unit in which the smoke evacuation shroud provides efficient smoke collection without obstructing the surgeon's view of the surgical site, and methods therefor.

Another object of this invention is to provide an improved smoke evacuation shroud apparatus for use with, but not limited to a laser surgical, an electro-surgical, or an ESU-argon beam coagulator pencil unit in which the smoke evacuation shroud provides efficient smoke removal by creating a vortex in the vicinity of the surgical site, and methods therefor.

BRIEF DESCRIPTION OF THE PREFERRED EMBODIMENTS

In accordance with one embodiment of this invention, an electro-surgical unit (ESU) pencil apparatus is disclosed comprising, in combination, cutting means for cutting and coagulating in a medical procedure, smoke evacuation means coupled to the cutting means for removing smoke and debris produced during the medical procedure, and telescopic member means coupled to the cutting means and to the smoke evacuation means for adjusting position of the cutting means and the smoke evacuation means along a lengthwise axis of the ESU pencil. It is well known in the art to provide cutting means that both cut and coagulate. The smoke evacuation means comprises a vacuum source, tubular member means coupled to the vacuum source for conveying the smoke and debris to the vacuum source, locking means coupled to the tubular member means and to the telescopic member means for holding a selected portion of the telescopic member means, and nozzle means coupled to the telescopic member means for evacuating the smoke and debris in proximity to a working site for the medical procedure. Additionally, the nozzle means has connection means for removably connecting the nozzle means to the telescopic member means. The telescopic member means comprises a tubular member slidably retained within conductive element means, conductive cap means coupled to a portion of the tubular member for conducting energy, conductive tang means, extending from a portion of the conductive cap means and contacting an inner surface portion of the conductive element means, for conducting the energy from the conductive element means to the conductive cap means, conducting member means supported within the tubular member for conducting the energy from the conductive cap means, conductive support means coupled between the conductive cap means and the conducting member means for conducting the energy from the conductive cap means to the conducting member means, electrode retainer means coupled to the conducting member means for retaining the cutting means and for transferring the energy to the cutting means, and vortex support means coupled to the conducting member means for supporting the conducting member means and for assisting formation of vortex flow of the smoke and debris. The ESU pencil apparatus further includes switch means for selectively applying the energy from an energy source via a connector to the conductive element means.

In accordance with another embodiment of this invention, an ESU-Argon beam coagulator pencil apparatus is disclosed comprising, in combination, cutting means for cutting in a medical procedure, coagulation means coupled to the cutting means for coagulating a patient's blood, smoke evacuation means coupled to the coagulation means for removing smoke and debris produced during the medical procedure, and telescopic member means coupled to the cutting means, the coagulation means, and the smoke evacuation means for adjusting position of the cutting means, the coagulation means, and the smoke evacuation means along a lengthwise axis of the pencil apparatus. The smoke evacuation means comprises a vacuum source, tubular member means coupled to the vacuum source for transferring the smoke and debris to the vacuum source, locking means coupled to the tubular member means and to the telescopic member means for holding a selected portion of the telescopic member means, and nozzle means coupled to the telescopic member means for evacuating the smoke and debris in proximity to a working site for the medical procedure. The nozzle means has connection means for slidably connecting the nozzle means to a portion of the telescopic member means and for forming a substantially air-tight connection between the nozzle means and the telescopic member means. The connection means includes notch means in a surface portion of the nozzle means for receiving a protrusion extending from a surface portion of the telescopic member means. The pencil apparatus further includes conductive element means coupled to an interior surface of the tubular member means for conducting energy supplied from an energy source. The telescopic member means comprises a tubular member slidably retained within the conductive element means, conductive cap means coupled to a portion of the tubular member for conducting the energy, conductive tang means, extending from a portion of the conductive cap means and contacting an inner surface portion of the conductive element means, for conducting the energy from the conductive element means to the conductive cap means, conducting member means supported within the tubular member for conducting the energy from the conductive cap means, conductive support means coupled between the conductive cap means and the conducting member means for conducting the energy from the conductive cap means to the conducting member means, electrode retainer means coupled to the conducting member means for retaining the cutting means and for transferring the energy to the cutting means, and vortex support means coupled to the conducting member means for supporting the conducting member means and for assisting formation of a vortex flow of the smoke and debris. The coagulation means comprises coagulating material supply, conduit means coupled to the coagulating material supply and to the hollow tube for conveying coagulating material from the coagulating material supply to the hollow tube, and delivery means coupled to the hollow tube for delivering the coagulating material to coagulate the blood. The coagulating material could be argon gas or other fluid. The delivery means comprises a tubular conduit extending through the nozzle means and beyond an end portion of the nozzle means, and the tubular conduit includes means for preventing suction of the coagulating material directly into the smoke evacuation means.

In accordance with yet another embodiment of this invention, an ESU pencil apparatus is disclosed comprising, in combination, a removable elongated shroud, adaptably fitted over the external surface of an ESU pencil apparatus, electro-surgical means located within a portion of the shroud and having electro-surgical tip means that extend below an opening located at a distal portion of the shroud for use in surgery, conduit means located within the elongated shroud having a tapered portion surrounding a portion of the electro-surgical means and in communication with the opening at the distal portion of the elongated shroud and an enlarged portion extending outwardly from the portion of the electro-surgical means and the tapered portion to a proximal opening in the elongated shroud for both increasing suction of smoke from the opening located at the distal portion of the shroud upwardly to the proximal opening in the elongated shroud and increasing visibility of the tip means below the opening in the distal portion of the shroud to permit better visualization of the surgery, external conduit means coupled to the proximal opening in the elongated shroud for exhausting smoke located within the shroud, and smoke evacuation means coupled to the external conduit means for exhausting smoke passing from the conduit means into the external conduit means.

In accordance with still another embodiment of this invention, a shroud for use with an ESU pencil apparatus is disclosed comprising, in combination, a removable elongated shroud, adaptably fitted over an external surface of the ESU pencil, electro-surgical means located within a portion of the shroud and having coagulation beam means coaxial with and surrounding retractable electro-surgical tip means that, when extended, reach below an opening located at a distal portion of the shroud for use in surgery, conduit means located within the elongated shroud having a tapered portion surrounding a portion of the electro-surgical means and in communication with the opening at the distal portion of the elongated shroud and an enlarged portion extending outwardly from the portion of the electro-surgical means and the tapered portion to a proximal opening in the elongated shroud for both increasing suction of smoke from the opening located at the distal portion of the shroud upwardly to the proximal opening in the elongated shroud and increasing visibility of the tip means below the opening in the distal portion of the shroud to permit better visualization of the surgery, external conduit means coupled to the proximal opening in the elongated shroud for exhausting smoke located within the shroud, and smoke evacuation means coupled to the external conduit means for exhausting smoke passing from the conduit means into the external conduit means.

In accordance with still another embodiment of this invention, a shroud apparatus for use with a surgical laser unit is disclosed comprising, in combination, a removable elongated shroud adaptably fitted over an external surface portion of the surgical laser unit, and having an opening in proximity to a tip portion of the removable elongated shroud, surgical laser means located within a portion of the elongated shroud for use in surgery, conduit means constrained by a tapered interior surface of the elongated shroud and in communication with the opening for both increasing suction of smoke from the opening to a proximal opening in the elongated shroud and for increasing visibility of the surgery, external conduit means coupled to the proximal opening in the elongated shroud for exhausting smoke located within the shroud, and smoke evacuation means coupled to the external conduit means for exhausting smoke passing from the conduit means into the external conduit means. The pencil apparatus further includes clamping means coupled to the elongated shroud for holding the surgical laser means. The tip portion of the elongated shroud extends beyond a portion of the clamping means for providing measuring means for establishing a minimum safe distance at which the surgical laser means can be operated in the surgery.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 1 is a perspective view of an ESU pencil apparatus according to the present invention, with the telescopic electrode assembly extended.

FIG. 2 is a perspective view of the apparatus in FIG. 1 with the telescopic surgical electrode assembly retracted.

FIG. 3 is an exploded view of the apparatus in FIG. 1.

FIG. 4 is a cross-sectional view of the apparatus in FIG. 1.

FIG. 5 is a cross-sectional view of an ESU-argon beam coagulator pencil apparatus in accordance with the present invention.

FIG. 6A is a side view of the electrode of the ESU pencil apparatus in FIG. 5.

FIG. 6B is a cross-sectional view of the nozzle of the ESU pencil apparatus in FIG. 5.

FIG. 6C is a cross-sectional view of the telescopic assembly of the ESU pencil apparatus in FIG. 5.

FIG. 7A is a cross-sectional view of the nozzle in FIG. 6B, taken along line 7A—7A.

FIG. 7B is a cross-sectional view of the nozzle in FIG. 6B, taken along line 7B—7B.

FIG. 7C is a cross-sectional view of the telescopic assembly in FIG. 6B, taken along line 7C—7C.

FIG. 7D is an enhanced view of the nozzle and distal end of the telescopic assembly, showing the locking mechanism for the nozzle of the ESU pencil apparatus in FIG. 5.

FIG. 8A is a perspective view of an ESU pencil apparatus and shroud in accordance with the present invention.

FIG. 8B is a perspective view of an extended nozzle for the ESU pencil apparatus in FIG. 8A.

FIG. 8C is a side view of an extended electrode with a blade tip for the ESU pencil apparatus in FIG. 8A.

FIG. 8D is a side view of a ball electrode tip for the ESU pencil apparatus in FIG. 8A.

FIG. 8E is a side view of a needle electrode tip for the ESU pencil apparatus in FIG. 8A.

FIG. 8F is an end view of the apparatus in FIG. 8A, taken from near the electrode tip.

FIG. 8G is an end view of another embodiment of the apparatus in FIG. 8A, taken from near the electrode tip.

FIG. 9A is a perspective view of an ESU-argon beam coagulator pencil apparatus and shroud, with the nozzle and electrode retracted, in accordance with the present invention.

FIG. 9B is a perspective view of the apparatus in FIG. 9A, with the nozzle and electrode extended.

FIG. 10A is a perspective view of another embodiment of the shroud for use with ESU-argon beam coagulator pencil apparatus, in accordance with the present invention.

FIG. 10B is a perspective view of another embodiment of an ESU-argon beam coagulator pencil apparatus with the shroud in FIG. 10A.

FIG. 11A is a perspective view of a laser surgical unit apparatus and shroud in accordance with the present invention.

FIG. 11B is a perspective view of the laser surgical unit apparatus in FIG. 11A.

FIG. 11C is a perspective view of a laser tip for use with the apparatus in FIG. 11B.

FIG. 11D is a perspective view of the shroud in FIG. 11A.

DESCRIPTION OF THE PREFERRED EMBODIMENTS

FIGS. 1, 2, 3 and 4 depict an electro-surgical unit (ESU) pencil apparatus 21 with a telescopic assembly 24. The tip of the electrode 12 is defined as the distal end of the ESU pencil apparatus 21 and the opposite end, the exhaust port 15, is defined as the proximal end. Hereafter in the specification, this definition is the reference for the use of the terms "distal end" and "proximal end" with respect to each element of the ESU pencil apparatus 21. The handpiece 22 has a locking cap 1 coupled to the distal end 25 of the handpiece 22 and an exhaust connector 13 attached to the proximal end 26 of the handpiece 22. The tubular inner surface of the handpiece 22 is lined with a cylindrical conducting element 3.

RF energy flows to the ESU pencil apparatus 21 from an RF source (not shown) via cord 14. Note that those skilled in the art refer to such an RF source as an ESU, and the working tool 21 is typically called an ESU pencil. On the outside of the handpiece 22 is a hand switch 4, which controls the supply of RF energy from the cord 14 to the conducting element 3. Note that it is well known in the art to supply RF energy of a first specification for cutting and RF energy of a different specification for coagulation. The switch 4 alternatively activates both type of RF energy.

The telescopic assembly 24 is contained within the conducting element 3. The outer diameter of the tubing 9, which forms the body of the telescopic assembly 24, is marginally smaller than the inner diameter of the conducting element 3, permitting the telescopic assembly 24 to slide along the longitudinal axis of the conducting element 3. A rod 5 is suspended inside the tubing 9 by means of two spacers 34 and 35. The plurality of fins 7 on the spacer 34 are slanted relative to the general direction of the flow of smoke and other fluids through the tubing 9, such that a vortex is created when the fluids flow past these fins 7. The rod 5, and the spacers 34 and 35, are made of conducting material. The socket 8 is located at the distal end of the spacer 34. The electrode 12 is removably coupled with the socket 8. Alternatively, the electrode 12 could be integral with the socket 8.

At the proximal end of the tubing 9 is the conductor cap 6. The conductor cap 6 is a thin tubular strip of metal that circles the outside of the proximal end 33 of the tubing 9, and allows fluid access to the inside of the tubing 9 from the proximal end 33. The outer surface of the tubing 9 at the proximal end 33 is slightly depressed so that the outer surface of the conductor cap 6 is flush with the outer surface of the tubing 9. The conductor cap 6 has electrical contact with the spacer 35. The spacer 35 is located at the proximal end 33 on the inside of the tubing 9. The conductor cap 6 has a plurality of tangs 23 that provide an electrical link between the conductor cap 6 and the conducting element 3.

At the distal end 32 of the tubing 9 is the nozzle 11. The nozzle 11 is hollow and tapered on its interior and exterior surfaces as viewed from near its proximal end 36 to its distal end 17. This tapering not only helps to increase the visibility of the tip of the electrode 12 and the site of the operation, but also increases the efficiency of the fluid removal from the operation site by creating an exhaust vortex near the operation site. Formation of the vortex is explained in detail later. Making the nozzle 11 from a transparent material further aids the visibility.

A portion near the proximal end 36 of the nozzle 11 is cylindrical and the outer diameter of the nozzle 11 is nearly equal to the inner diameter of the tubing 9 so that a substantially air-tight connection is formed when the proximal end 36 of the nozzle 11 is inserted into the distal end 32 of the tubing 9. A locking mechanism is also provided to secure the connection between the nozzle 11 and the tubing 9. The pin 16 on the nozzle 11 is designed to fit into the L-shaped slot 37 at the distal end 32 of the tubing 9. A secure connection is made by sliding the pin 16 into the slot 37 and twisting the nozzle 11. An alternative embodiment of the telescopic assembly 24 would have the nozzle 11 as an integral part of the tubing 9.

The telescopic assembly 24 is held in position within the handpiece 22 by the locking cap 1. The exterior of the locking cap 1 is conical at the distal end and substantially tubular at the proximal end. However, the inside of the locking cap 1 is hollow and cylindrical. The inner diameter of the locking cap 1 is only marginally greater than the outer diameter of the tubing 9.

The tubing 9 passes through the locking cap 1. The locking cap 1 is designed to connect to the distal end 25 of the handpiece 22, with the locking cap threads 27 engaging the handpiece threads 28. The locking cone 30 on the inner surface of the handpiece 22 is conical with the diameter at the proximal end 31 of the locking cone 30 being less than that at the distal end of the locking cone. As the locking cap 1 is screwed into the distal end 25 of the handpiece 22, the slotted flanges 29 at the proximal end of the locking cap 1 press into the decreasing diameter of the locking cone 30. Thus, the flanges 29 are pressed inward by the decreasing inner diameter of the locking cone 30, securing the telescopic assembly 24 to the handpiece 22.

The distal end of the exhaust connector 13 fits into the proximal end 26 of the handpiece 22. The sleeve 38, at the distal end of the connector 13, is of marginally lesser outer diameter than the inner diameter of the proximal end 26 of the handpiece 22, so that a substantially air-tight connection between the sleeve 38 and the handpiece 22 is formed. Note, threaded engagement or other means of connecting well known in the art are acceptable to connect the exhaust connector 13 to the handpiece 22. Alternatively, the exhaust connector 13 could be integral with the proximal end 26 of the handpiece 22. At the proximal end of the connector 13 is the exhaust port 15 that is connected to suction tubing (not shown).

FIGS. 5, 6A–C, and 7A–C depict an ESU-Argon beam coagulator pencil apparatus 121 with telescopic assembly 124, in accordance with the present invention. The tip of the electrode 112 is defined as the distal end of the ESU-argon beam coagulator pencil apparatus 121 and the opposite end, the exhaust port 164, is defined as the proximal end. As previously explained, the ends of all other elements of the ESU-argon beam coagulator pencil apparatus 121 are referenced with respect to this definition of the distal and proximal ends.

The handpiece 122 has a locking cap 101 coupled to the distal end of the handpiece 122. An exhaust connector 113 is coupled to the proximal end of the handpiece 122. The handpiece 122 is similar to the earlier mentioned handpiece 22, except that the handpiece 122 has an additional hand switch 150 for regulating the supply of coagulating material to the inlet port 162. While the invention has been particularly described with argon gas as the inert material supplied, other inert fluids too could be supplied as the inert material. The inside of the handpiece 122 is lined with a cylindrical conducting element 103. On the outside of the handpiece 122 are two hand switches 104 and 150. Handswitch 104 regulates the supply of RF energy from an RF source (not shown) via a cord 114 to the conducting element 103. Hand switch 150 regulates the flow of argon to the inlet port 162.

The telescopic assembly 124 (shown in greater detail in FIG. 6C) is contained within the conducting element 103. The telescopic assembly 124 is similar to the previously described telescopic assembly 24. The outer diameter of the cylindrical tubing 109, which forms the body of the telescopic assembly 124, is marginally smaller than the diameter of the conducting element 103, permitting the telescopic assembly 124 to slide along the longitudinal axis of the conducting element 103. A thin hollow rod 105 is suspended inside the tubing 109 by means of two spacers 134 and 135. The plurality of fins 107 on the spacer 134 are slanted relative to the longitudinal axis of the tubing such that a vortex is created when smoke and other fluids flow past the fins 107. The socket 108 is located inside the distal end of the rod 105. The spacers 136 and 137 suspend the socket 108 inside the rod 105. The electrode 112 is removably coupled with this socket 108. Alternatively, the electrode 112 could be integral with this socket 108. The rod 105, and the spacers 135, 136, and 137 are made of conducting material.

At the proximal end of the tubing 109 is the conductor cap 106. It is a thin tubular strip of metal that circles the outside of the proximal end of the tubing 109, and allows fluid access to the inside of the tubing 109 from the proximal end of the tubing 109. The outer surface of the tubing 109 at the proximal end is slightly depressed so that the outer surface of the conductor cap 106 is flush with the outer surface of the tubing 109. The conductor cap 106 has an electrical contact with the spacer 135. The spacer 135 is located at the proximal end on the inside of the tubing 109. The conductor cap 106 has a plurality of tangs 123 that provide an electrical link between the conductor cap 106 and the conducting element 103.

Coupled to the distal end of the tubing 109 is the nozzle assembly 111. The nozzle 151 forms the exterior of the nozzle assembly 111. The distal section of the nozzle 151 is conical, whereas the proximal section of the nozzle 151 is cylindrical At the distal end of the nozzle 151 is an aperture, and the diameter of the aperture increases towards the middle of the nozzle 151. From about the middle of the nozzle 151 to its proximal end, the nozzle is cylindrical. The inner diameter of the proximal end of the nozzle 151 is marginally larger than the outer diameter of the tubing 109 such that there is a substantially air-tight connection between the two, and yet the nozzle 151 can slide freely over the tubing 109.

The tapering of the distal section of the nozzle 151 not only helps to increase the visibility of the tip of the electrode 112 and the site of the operation, but also increases the efficiency of the fluid removal from the operation site by creating an exhaust vortex near the operation site. Formation of the vortex is explained in detail later. Making the nozzle 151 from a transparent material further aids the visibility.

A locking mechanism (shown more clearly in FIG. 7D) prevents the nozzle from accidentally slipping out from over the telescopic assembly 124. The locking mechanism is comprised of a U-shaped channel 120, and a locking tab 102. The channel 120 is cut on the inner surface of the nozzle 151. The locking tab 102 is a protrusion located near the distal end of the tubing 109 and runs in the channel 120 when the nozzle 151 is coupled to the tubing 109. The channel 120 has two legs 161 and 165, running circumferentially around the longitudinal axis of the nozzle 151. A bridge 163, running longitudinally, connects the two legs. The leg 165 traverses a substantial distance along the inner circumference of the nozzle and has access from the proximal edge of the nozzle 151. The termination of the leg 165 at the proximal end of the nozzle 151 forms a loop to prevent the locking tab from accidentally slipping out of the channel 120.

When the nozzle assembly 111 is inserted over the telescopic assembly 124 the locking tab 102 is maneuvered into the leg 165. When the nozzle assembly 111 is to be slid to and fro relative to the telescopic assembly 124, the locking tab 102 moves in the bridge 163 of the channel 120. When the locking tab 102 is in leg 161, the mouth 154 will cover the tip of the electrode 112. To remove the nozzle assembly 111, the locking tab 102 is maneuvered past the loop of the leg 165. Note, other forms of locking mechanisms known in the art are also acceptable for locking the nozzle assembly 111 over the telescopic assembly 124.

Another component of the nozzle assembly 111 is a tubular argon conduit 152 located inside the nozzle 151. The conduit 152 is substantially cylindrical. The diameter of the conduit 152 is marginally larger than that of the rod 105 such that a substantially air-tight, yet slidable, connection is formed when the distal end of the rod 105 is inserted into the proximal end of the conduit 152. A plurality of spacing vanes 153 are attached to the outer surface of the conduit 152 so as to suspend the conduit 152 inside the nozzle 151. Further, these spacing vanes 153 are slanted relative to the axial flow of smoke and other fluids through the nozzle assembly 111 so as to create a vortex flow. The mouth 154 of the conduit 152 extends beyond the distal end of the nozzle 151. The mouth 154 flares out to prevent the argon gas coming out of the conduit 152 from being immediately drawn into the smoke duct 155.

The locking cap 101 is similar to the previously discussed locking cap 1. As the locking cap 101 is screwed into the distal end of the handpiece 122, the cap 101 will circumscribe a portion of the telescopic assembly 124 and lock the telescopic assembly 124 into place.

The distal end of the connector 113 is designed to fit into the proximal end of the handpiece 122. A sleeve 138, at the distal end of the connector 113 is of narrower outer diameter than the inner diameter of the proximal end of the handpiece 122, such that the sleeve 138 forms a tight seal when inserted into the proximal end of the handpiece 122. Note, threaded engagement or other means of connecting well known in the art may be implemented to connect the exhaust connector 113 to the handpiece 122. Alternatively, the connector 113 could be integral with the handpiece 122.

At the proximal end of the connector 113 are two ports— the exhaust port 164 and the inlet port 162. The exhaust port 164 is connected to a suction source (not shown) via tubing (not shown), and the inlet port 162 is connected to an argon supply (not shown). Inside the inlet port 162 is a long, narrow, tubular member 160, whose distal end is inserted into the proximal end of the rod 105. The outer diameter of the tubular member 160 is marginally less than the inner diameter of the rod 105 such that a substantially air-tight, yet slidable connection is made between the tubular member 160 and the rod 105 when the tubular member 160 is partially inserted into the rod 105. The length of the tubular member 160 is sufficient as to ensure uninterrupted flow of argon gas even when the telescopic assembly 124 is fully extended from the handpiece 122.

FIGS. 6A–C and 7A–C depict some of the elements of the ESU pencil apparatus shown in FIG. 5. FIG. 6A depicts a side view of the electrode 112. FIG. 6B depicts a cross-sectional view of the nozzle assembly 111. FIG. 6C depicts a cross-sectional view of the telescopic assembly 124. FIG. 7A depicts the cross-sectional view of the nozzle assembly 111 taken through the spacing vanes 153. FIG. 7B is an cross-sectional view near the proximal end of the nozzle assembly 111. FIG. 7C is an cross-sectional view from near the distal end of the telescopic assembly 124.

FIGS. 8A–G show another embodiment of an ESU pencil apparatus 402 and smoke evacuation assembly or shroud 410 according to the present invention. This embodiment adopts the smoke evacuation assembly (hereinafter shroud) 410 for use with electrodes 406 of various lengths. The handpiece holder 421 is shaped to hold the handpiece 405 of an ESU pencil apparatus 402. The tip of the electrode 406 passes through electrode opening 422, the nozzle 412, and the exhaust opening 424. The electrode opening 422 is shaped to substantially conform to the distal end of the handpiece 405. The electrode opening 422 not only helps to support the ESU pencil apparatus 402, but also forms a substantially airtight seal around the contacting surface portion of the handpiece 405. Handswitch 404 regulates the RF supply to the electrode 406.

The nozzle 412 is detachably coupled to the connecting neck 426 of the shroud 410. Alternatively, the nozzle 412 could be integral to the shroud 410. The passageway 428 inside the nozzle 412, while quite narrow at the exhaust opening 424, widens sharply towards the connecting neck 426. The chute 420 is located alongside the handpiece holder 405, and forms a path between the exhaust port 416 and the passageway 428. The exhaust port 416 connects the chute 420 to a suction source (not shown).

The tapering of the passageway 428 not only helps to increase the visibility of the tip of the electrode 406 and the site of the operation, but also increases the efficiency of the fluid removal from the operation site by creating an exhaust vortex near the operation site. Formation of the vortex is explained in detail later. Making the nozzle 412 from a transparent material further aids the visibility.

When an extended electrode 430 (FIG. 8C), needs to be used with the ESU pencil apparatus 402, the exhaust opening 424 will be too far from the blade tip 436 to establish an effective exhaust flow in proximity of the blade tip 436. In such circumstances, the nozzle 412 is detached from the shroud 410, and is replaced with elongated nozzle 425 (FIG. 8B). The extended electrode 430 has a spacer 432 with a plurality of fins 434 that help stabilize the extended electrode 430 within the elongated nozzle 425. If slanted to the general direction of the fluid flow through the elongated nozzle 425, the fins 434 could be used to increase the efficiency of the vortex created by the venturi effect of the elongated nozzle 425. Note that there are many different angles at which the fins 434, or any other fins herein may be situated to assist vortex flow. The tip of the extended electrode 430 could be of different types—for example, a blade electrode (436—FIG. 8C), ball electrode (440—FIG. 8D), or a needle electrode (450—FIG. 8E).

FIGS. 8F and 8G depict the end views of two embodiments of the present invention. These end views are taken from near the tip of the electrode 406. FIG. 8F is the end view of the apparatus shown in FIG. 8A. Here, the side of the chute 420 adjacent to the handpiece holder 421 is shaped to conform substantially to the shape of the handpiece holder 421. FIG. 8G is the end view of a apparatus according to the present invention in which the chute 423 is substantially cylindrical.

Whereas FIGS. 8A–G show adaptation of the invention for use with a ESU pencil apparatus 402, FIGS. 9A–B, and 10A–B show two more embodiments of the present invention for use with two types of ESU-argon beam coagulator pencils 502 and 602. FIGS. 9A–B show the adaptation of the shroud 510 for use with an ESU-argon beam coagulator pencil apparatus 502. In ESU-argon beam coagulator pencil apparatus 502 the argon beam (for coagulation) surrounds the electrode 506. The electrode 506 is activated by handswitch 503, and the argon beam by handswitch 504. The bolt 501 allows the electrode 506 to be extended (see FIG. 9B) and retracted (see FIG. 9A). The exhaust port 516 connects the shroud 510 to a suction source (not shown) via a smoke evacuation channel (not shown).

The nozzle 512 is tapered and preferably made of transparent material. This helps to increase the visibility of the operation site and of the tip of the electrode 506. The smoke and other fluids from the operation site enter the nozzle through a narrow opening at the tip 524 and proceed into a wider passageway inside the nozzle 512. The resultant venturi effect increases the efficiency of fluid removal from the operation site by creating an exhaust vortex near the operation site. Formation of the vortex is explained in detail later.

A novel feature of shroud 510 is the adjustable nozzle 512. A portion of the nozzle 512 is designed to slide within a neck piece 513 and lock in two extreme positions—one retracted (see FIG. 9A) and the other extended (see FIG. 9B). When the nozzle 512 is retracted, it exposes the argon conduit tip 532. When the nozzle 512 is extended, the tip of the nozzle 524 covers the argon conduit tip 532, and is designed to be near the blade tip 507 of the extended electrode 506, thus ensuring an efficient smoke removal near the blade tip 507.

FIGS. 10A–B illustrate the adaptation of the shroud 610 for use over an ESU-argon beam coagulator pencil apparatus 602 in which the argon conduit 630 is set apart from electrode 606. FIG. 10A shows just the shroud 610, and 10B shows the shroud 610 fitted over the ESU-argon beam coagulator pencil apparatus 602. Handswitch 604 controls the RF energy supply to the electrode 606, and handswitch 603 controls the argon supply. The bolt 601 allows the electrode 606 to be extended and retracted. A suction source, for removing the smoke from the site of the operation, is applied to the shroud 610 through the exhaust port 616. The electrode passes through the nozzle 612. The tapered nozzle 612 once again produces a vortex around the tip of the electrode 606. A conduit access 628 fits around the conduit 630.

FIGS. 11A–D show the adaptation of the shroud 710 for use with a laser surgery pencil apparatus 702. The laser surgery pencil apparatus 702 is depicted in FIG. 11B, and the shroud 710 is depicted in FIG. 11D. The handpiece 704 of the laser surgical pencil apparatus 702 is generally of conical shape, but the shape of the handpiece is not a constraint for adaptation of the present invention. Near the handpiece tip 705 of the laser surgery pencil apparatus 702 is a cylindrical neck 706. When the handpiece 704 is used without the shroud 710, the clip 709 of focusing cap 707 (see FIG. 11C) fits over the neck 706 and tip 708 of the focusing cap 707 marks the minimum safe operating point of the laser surgical pencil apparatus 702

When laser surgical pencil apparatus 702 is used with the shroud 710, the focusing cap 707 is removed from the neck 706 and the neck 706 is inserted into the passage 728 inside the holder 726 (see FIG. 11D). The shroud 710 fits around the laser surgical pencil apparatus 702 with the clamp 721 securing the head 730 of the laser surgical pencil apparatus 702. A groove 722 in the clamp 721 locks around the cleaning gas inlet 732 so as to provide more stability to the fitting of the shroud 710 around the laser surgical pencil apparatus 702. The shroud tip 725 provides measurement of the minimum safe operation point for the laser surgical pencil apparatus 702.

The smoke inlet 724 is located near the shroud tip 725. An alternate embodiment would be to have more than one shroud tip 725, each with its own smoke inlet 724. The smoke inlet 724 is narrow and opens into a relatively wider exhaust chute 720, which steadily widens as it moves away from the smoke inlet 724. At the other end of the passageway is the exhaust port 716, which is connected to a suction apparatus (not shown).

A venturi effect on the fluid passing through the smoke inlet 724 increases the efficiency of the fluid removal from the operation site by creating an exhaust vortex near the operation site. Formation of the vortex is explained in detail later. Making the shroud tip 725 from a transparent material further aids the visibility.

OPERATION

Referring to FIGS. 1, 2, 3 and 4, the RF supply (not shown) to the ESU pencil apparatus 21 is controlled by means of the hand switch 4. The RF energy flows from cord 14 to the conducting element 3. From the conducting element 3, the RF energy reaches the conductor cap 6 through the tangs 23. The tangs 23 press against the conducting element 3. Because the conducting element 3 extends over the range of motion for the tangs 23 along the longitudinal axis of the telescopic assembly 24, the electrical contact between the tangs 23 and the conducting element 3 is continuous. From the conductor cap 6, the RF energy passes on to the spacer 35, the rod 5, spacer 34, and the electrode 12.

The smoke and other debris created during the surgical procedure is removed through the exhaust connector 13, located at the proximal end 26 of the handpiece 22. The smoke is sucked out from the exhaust connector 13 by suction means (not shown) such as a vacuum pump, via suction tubing (not shown) that is connected to exhaust port 15. The passageway for the smoke and other fluids from the site of the operation to the exhaust port 15 is as follows: the fluids enter the ESU pencil apparatus 21 through the distal end 17 of the nozzle 11. The fluids then flow past the spacer 34, the rod 5, the spacer 35, the handpiece 22, and enter the exhaust connector 13. The locking cap 1, which is coupled with the handpiece 22, forms an airtight-seal with the handpiece 22, and the slotted flanges 29 fit tightly over the tubing 9 forming another airtight connection with the outer surface of the tubing 9. These airtight connections prevent air flow through the annular space between the conducting element 3 and the outer surface of the tubing 9.

The tapered shape of the nozzle 11 not only increases the visibility of the area being operated upon but also increases the efficiency of the smoke removal from the operation site. Since the distal end 17 of the nozzle 11 leads into a wider passageway inside the nozzle 11, a venturi effect causes an acceleration of these fluids as they pass through the distal end 17. The pressure drop in the passageway immediately beyond the distal end 17 is large enough to produce a spiraling or "vortex" fluid flow through the nozzle 11. This vortex soon extends to surround the tip of the electrode 12. The vortex increases the efficiency of the smoke removal. The vortex is enhanced by the spacer 34 since the plurality of fins 7 is angled to the general direction of the flow of the fluids. Note, while providing structures(such as fins 7) inside the passageway of the fluids can enhance the efficiency of the vortex, such structures are not a requirement for the creation of a vortex.

When the surgeon desires to change the distance of the tip of the electrode 12 from the handpiece 22, the locking cap 1 is loosened. This releases the grip of the locking cap 1 on the telescopic assembly 24, and it may now be extended or retracted as desired. When the desired length is reached, the locking cap 1 is tightened again, and the telescopic assembly 24 is locked into position. Since the distal end 17 is always near the tip of the electrode 12 irrespective of the position of the telescopic assembly 24 within the hand piece 22, the efficiency of smoke removal is not effected by the sliding of the telescopic assembly 24. Depending on how much of the tip of the electrode 12 the surgeon desires to have exposed, a nozzle 11 of appropriate size and shape may be used. After the operation, the electrode 12, the telescopic assembly 24, the nozzle 11, and locking cap 1 are disposed of, but the handpiece 22 and exhaust connector 13 may be reused.

Referring to FIGS. 5, 6A–C, and 7A–C, a major additional feature introduced in this embodiment is the argon beam, whose activation is controlled through the hand switch 150. The argon beam is conveyed to the site of the surgical procedure through the inlet port 162, the tubular member 160, the rod 105, conduit 152 and finally the mouth 154. The unique shape of the mouth 154 of the conduit 152 shields the argon beam from the exhaust suction, as will be explained below.

Smoke and other fluids from the operation site are removed through the smoke duct 155 by coupling a suction source (not shown) to the exhaust port 164. Smoke and other fluids from the operation site are sucked into the smoke duct 155 through the annular space between the mouth 154 of the conduit 152 and the tip 117 of the nozzle 151. As previously explained, since the distal end of the smoke duct 155 tapers, and since the entrance to the smoke duct 155 is narrow, the venturi effect produced creates a vortex around the site of the operation. The plurality of spacing vanes 153 near the tip 117 are angled to the direction of the flow of the smoke and thus aid in the creation of the vortex.

In the absence of the mouth 154, the suction from the smoke duct 155 would tend to draw the argon beam directly into the smoke duct 155 prior to reaching the operation site, because the inlet of the smoke duct 155 surrounds the conduit 152 (i.e. argon beam outlet). This is a problem that prior technology has been unable to solve. Now, this problem has been solved by having the outlet of the argon beam passageway (i.e. the mouth 154 of the conduit 152) extend a little beyond the inlet of the smoke duct 155 (i.e. the tip 117 of the nozzle 151),and having the mouth 154 flare out. The mouth 154 deflects the exhaust vortex made by the smoke duct 155, and forms an eye of relative calm in the middle of the vortex. Since the tip of the electrode 112 is located in the middle of this calm, the argon beam proceeds unhindered to the site of the operation. As smoke is created as a result of the operation, it will be pushed outward by the argon beam, where it will be captured by the exhaust vortex.

Sliding the nozzle assembly 111 over the tubing 109 enables the surgeon to vary the length of the tip of the electrode 112 that the surgeon desires to expose. The range of movement for the nozzle assembly 111 is determined by the locking mechanism. The locking tab 102 of the locking mechanism moves along the bridge 163 of the channel 120, and the loop on the leg 165 prevents the nozzle 151 from accidentally slipping out from over the tubing 109.

The working of the telescopic assembly 124 is similar to that explained earlier for the telescopic assembly 24. The smoke is conveyed from the operation site through the smoke duct 155, the tubing 109, the handpiece 122, the exhaust connector 113, and through the exhaust port 164.

The ESU-argon beam coagulator pencil apparatus 121 may be used in three possible modes—as an ESU pencil for cutting and coagulation (without argon beam), as an argon-beam enhanced ESU pencil for cutting and coagulation, and as a pure argon beam coagulator. When the ESU-argon beam coagulator pencil apparatus 121 is to be used for cutting and coagulation without the argon beam, the RF hand switch 104 is alternatively placed in the cutting and coagulation positions, while the argon hand switch 150 remains in the off position. The nozzle assembly 111 is adjusted (by moving the nozzle assembly 111 to and fro) over the telescopic assembly 124 to expose the desired length of the electrode 112. The nozzle assembly 111 is positioned over the telescopic assembly 124 so as to maximize the suction on the operation site without hampering visibility of the tip of the electrode 112 or of the operation site. The optimal position of the nozzle 111 is a matter of personal preference of the surgeon.

When the ESU-argon beam coagulator pencil apparatus 121 needs to be used as an argon-beam coagulation enhanced ESU pencil for cutting and coagulation, then the RF hand switch 104 is alternatively placed in the cutting or coagulation position, and the argon hand switch 150 is switch on. The nozzle assembly 111 is adjusted to maximize the efficiency of the argon beam, the efficiency of the removal of the smoke and other fluids from the site of the operation, and the visibility of both the tip of the electrode and the site of the operation. The optimal position of the nozzle ill, once again, is dictated by the personal preference of the surgeon.

In the final mode, when the ESU-argon beam coagulator pencil apparatus 121 needs to be used purely as an argon-beam coagulator, the RF hand switch 104 is switched to the coagulation position, and the argon hand switch 150 is switch on. Because the electrode 112 is not required for this procedure, the nozzle assembly 111 is moved out to cover the tip of the electrode. To lock the nozzle assembly 111 in this position, the locking tab 102 is maneuvered into the leg 161 of channel 120. Now the mouth 154 of the conduit 152 becomes the distal tip of the whole ESU-argon beam coagulator 121. This allows the argon beam to be released very close to the site of the procedure, thereby maximizing the efficiency of the argon beam. Suction is used to remove smoke and other fluids created during the coagulation.

Referring to FIGS. 8A–G, the ESU pencil apparatus 402 is mounted in the handpiece holder 421 of the shroud 410. A suction source (not shown) is coupled to the shroud 410 through the exhaust port 416. The smoke and other fluids from the operation site are sucked into the passageway 428 inside the nozzle 412 through the exhaust opening 424. The chute 420 conveys smoke and other debris from the passageway 428 to a debris collector (not shown) via the exhaust port 416 and the smoke evacuation channel (not shown).

Since the narrow exhaust opening 424 leads into a wider passageway 428 inside the nozzle 412, the nozzle 412 produces a venturi effect on the fluids flowing into the nozzle 412, causing an acceleration of these fluids as they pass through the exhaust opening 424. Further, the pressure drop in the passageway 428 immediately beyond the exhaust opening 424 is large enough to produce a spiraling or "vortex" fluid flow through the nozzle 412. This vortex soon extends to surround the tip of the electrode 406. Note, while providing structures (such as vanes) inside the passageway 428 can enhance the efficiency of the vortex, such structures are not a requirement for the creation of a vortex. Since the passageway 428 widens sharply from the exhaust opening 424 towards the connecting neck 428, the pressure lost in the passageway 428 is minimal.

Nozzle 412 is replaced with the elongated nozzle 425 when the extended electrode 430 is to be used with the ESU pencil apparatus 402. This permits efficient collection of the fluids from near the blade tip 436. As explained previously, a vortex is created by the venturi effect at the entrance of the nozzle 425. Further, the slanted fins 434 augment the vortex created by the venturi effect.

FIGS. 9A–B, and 10A–B show two more embodiments of the present invention for use with two types of ESU-argon beam coagulator pencils. FIGS. 9A–B show the adoption of the shroud 510 for use with an ESU pencil apparatus 502 which has an argon beam (for coagulation) surrounding the electrode 507. A suction source (not shown) is coupled to the shroud 510 through the exhaust port 516. Since the smoke inlet 524 is narrow and opens into a relatively wider passageway inside the nozzle 512, a venturi effect causes the fluids passing through the smoke inlet 524 to accelerate. As explained earlier, when the smoke and other fluids accelerate through the smoke inlet 524, the rushing fluids spirals and form a vortex. This vortex increases the efficiency of the evacuation of the fluids generated at the site of the operation In FIG. 9A, when the electrode 506 is retracted, the ESU pencil apparatus 502 is to be used purely as an argon beam coagulator. The RF hand switch 503 is set to the coagulation position and the argon hand switch 504 is turned on. The suction source (not shown) is also turned on to remove smoke and other fluids produced during the coagulation process. The nozzle 512 is retracted, so that the conduit tip 532 extends beyond the nozzle tip 524 thereby permitting uninterrupted passage of the argon beam from the argon conduit 530 to the operation site. Now, if the electrode 506 is extended, and the the RF switch 503 is alternatively placed in cutting and coagulation positions, the cutting and coagulation functions of the ESU pencil apparatus is enhanced by the argon beam.

In FIG. 9B, the ESU pencil apparatus 502 is to be used as a normal ESU pencil (i.e. without an argon beam). The electrode 506 and the nozzle 512 are extended. The RF hand switch 503 is alternatively placed in the cutting and coagulation positions, and the argon hand switch 504 is switch off.

The operation of the apparatus in FIGS. 10A–B is similar to that explained above for the apparatus in FIGS. 9A–B. The shroud 610 has been adapted for use with an ESU pencil apparatus 602 which has an argon beam (for coagulation) set apart from the electrode 606.

A suction source (not shown) is coupled to the shroud 610 through the exhaust port 616. As explained earlier, the venturi effect accelerates the smoke and other fluids through the smoke inlet 624 and forms a vortex around the electrode 606. This vortex increases the efficiency of the evacuation of the fluids generated at the site of the operation When the electrode 606 is retracted, the ESU pencil apparatus 602 is to be used purely as a coagulator. When the ESU pencil apparatus 602 is used for cutting, the electrode 606 is extended. The suction source (not shown) is switched on, and the argon supply switch 504 is turned off. When the ESU pencil apparatus 602 is to be used simultaneously as both an ESU pencil for cutting and an argon beam coagulator (as an "argon beam coagulator enhanced ESU cutting pencil"), the electrode 606 is extended. The RF hand switch 603 is set to cut, and the argon hand switch 604 is turned on. The nozzle 612 shield the argon beam from the suction.

Referring to FIG. 11A–D, the present invention has been adapted to work with a laser surgical pencil apparatus 702. A suction source (not shown) is applied to the exhaust port 716 which sucks in smoke and other fluids into the smoke inlet 724 from site of the operation. Since the smoke inlet 724 is narrow and opens into a relatively wider exhaust chute 720, a venturi effect causes the fluids passing through the smoke inlet 724 to accelerate. As explained earlier, when the smoke and other fluids accelerate through the smoke inlet 724, the rushing fluids spirals and form a vortex. This vortex increases the efficiency of the evacuation of the fluids generated at the site of the operation.

While the invention has been particularly shown and described with reference to the preferred embodiments thereof, it will be understood by those skilled in the art that the foregoing and other changes in form and details may be made therein without departing from the spirit and scope of the invention. For example, any of the previous embodiments of the invention may be modified to include a means for regulating the suction applied to remove the smoke and other fluids from the site of the operation. Also, if desired, a telescopic member could be achieved by using a screw type arrangement, a rack and pinion arrangement, or a series of notches and corresponding protrusion, as suggested by the nozzle arrangement in FIG. 7D.

What is claimed is:

1. An electro-surgical unit (ESU)-Argon beam coagulator pencil apparatus comprising, in combination:

cutting means for cutting and coagulation in a medical procedure;

coagulation means coupled to said cutting means for coagulating a patient's blood;

smoke evacuation means coupled to said coagulation means for removing smoke and debris produced during said medical procedure; and telescoping means coupled to said cutting means, said coagulation means, and said smoke evacuation means for adjusting position of said cutting means, said coagulation means, and said smoke evacuation means along a lengthwise axis of said apparatus.

2. The apparatus of claim 1 wherein a lengthwise axis of said cutting means is coaxial with a lengthwise axis of said coagulation means, and said lengthwise axis of said coagulation means is coaxial with a lengthwise axis of said smoke evacuation means.

3. The apparatus of claim 1 wherein said smoke evacuation means comprises:

a vacuum source;

a tubular member coupled to said vacuum source for transferring said smoke and debris to said vacuum source;

locking means coupled to said tubular member and to said telescoping means for holding a selected portion of said telescoping means; and a nozzle coupled to said telescoping means for evacuating said smoke and debris in proximity to a working site for said medical procedure.

4. The apparatus of claim 3 wherein said nozzle has connection means for slideably connecting said nozzle to a portion of said telescoping means and for forming a substantially air-tight connection between said nozzle and said telescoping means.

5. The apparatus of claim 4 wherein said connection means includes notching means in a surface portion of said nozzle for receiving a protrusion extending from a surface portion of said telescoping means.

6. The apparatus of claim 3 wherein a portion of said nozzle means has a tapered inner and outer surface area.

7. The apparatus of claim 6 wherein said tapered inner surface area of said nozzle assists in forming vortex flow of said smoke and debris into and through said pencil apparatus.

8. The apparatus of claim 3 wherein an external surface portion of said locking means has a threaded portion for engagement with another threaded portion on an internal surface portion of said tubular member.

9. The apparatus of claim 8 wherein said tubular member has a tapered inner surface area portion in proximity to said another threaded portion.

10. The apparatus of claim 9 wherein said locking means has a tubular portion having a serrated edge for clamping around said selected portion of said telescoping means when said tapered inner surface are portion of said tubular member forces said serrated edge around said selected portion of said telescoping means as said locking means is inserted into said tubular member.

11. The apparatus of claim 3 further including a conductive element coupled to an interior surface of said tubular member for conducting energy supplied from an energy source.

12. The apparatus of claim 11 wherein said conductive element comprises a second tubular member extending substantially the full length of said tubular member.

13. The apparatus of claim 11 wherein said telescoping means comprises:

a tubular member slideably retained within said conductive element;

a conductive cap coupled to a portion of said tubular member for conducting said energy;

a conductive tang, extending from a portion of said conductive cap and contacting an inner surface portion of said conductive element, for conducting said energy from said conductive element to said conductive cap;

a conducting member supported within said tubular member for conducting said energy from said conductive cap;

conductive support means coupled between said conductive cap and said conducting member for conducting said energy from said conductive cap to said conducting member;

electrode retainer means coupled to said conducting member for retaining said cutting means and for transferring said energy to said cutting means; and vortex support means coupled to said conducting member for supporting said conducting member and for assisting formation of a vortex flow of said smoke and debris.

14. The apparatus of claim 13 wherein said conducting member is a hollow tube.

15. The apparatus of claim 14 wherein said coagulation means comprises:

coagulating material supply;

a conduit coupled to said coagulating material supply and to said hollow tube for conveying coagulating material from said coagulating material supply to said hollow tube; and delivery means coupled to said hollow tube for delivering said coagulating material to coagulate said blood.

16. The apparatus of claim 15 wherein said delivery means comprises a tubular conduit extending through said nozzle and beyond an end portion of said nozzle means.

17. The apparatus of claim 16 wherein said tubular conduit includes means for preventing suction of said coagulating material directly into said smoke evacuation means.

18. The apparatus of claim 17 wherein said means for preventing said suction of said coagulating material directly into said smoke evacuation means comprises an annular end portion of said tubular conduit angled away from a lengthwise axis of said tubular conduit.

19. The apparatus of claim 15 wherein adjusting said telescoping means changes both volume of tubular cavity means for carrying said smoke and debris, and volume of cylindrical cavity means coaxial with said tubular cavity means for delivering said coagulating material.

20. The apparatus of claim 15 further including switching means for selectively supplying said coagulating material.

21. The apparatus of claim 11 further including switching means for selectively applying said energy from said energy source via a connector to said conductive element.

22. A method of operating an electro-surgical unit (ESU)-Argon beam coagulator pencil apparatus comprising the steps of:

coupling cutting means to said apparatus for cutting and coagulation in a medical procedure;

coupling coagulation means to said cutting means for coagulating a patient's blood;

coupling smoke evacuation means to said coagulation means for removing smoke and debris produced during said medical procedure; and moving a telescoping means coupled to said cutting means, said coagulation means, and said smoke evacuation means for adjusting position of said cutting means, said coagulation means, and said smoke evacuation means along a lengthwise axis of said pencil apparatus.

* * * * *